(12) United States Patent
Alpire et al.

(10) Patent No.: US 12,282,012 B2
(45) Date of Patent: Apr. 22, 2025

(54) METHOD, SYSTEM AND PAPERBOARD PRODUCTION MACHINE FOR ESTIMATING PAPERBOARD QUALITY PARAMETERS

(71) Applicant: Siemens Aktiengesellschaft, Munich (DE)

(72) Inventors: Adam Alpire, Erlangen (DE); Thomas Eisenstecken, Erlangen (DE); Michael Hildebrand, Erlangen (DE); Ferdinand Kisslinger, Hersbruck (DE)

(73) Assignee: Siemens Energy Global GmbH & Co. KG, Munich (DE)

( * ) Notice: Subject to any disclaimer, the term of this patent is extended or adjusted under 35 U.S.C. 154(b) by 470 days.

(21) Appl. No.: 17/636,865

(22) PCT Filed: Aug. 19, 2020

(86) PCT No.: PCT/EP2020/073139
§ 371 (c)(1),
(2) Date: Feb. 19, 2022

(87) PCT Pub. No.: WO2021/037615
PCT Pub. Date: Mar. 4, 2021

(65) Prior Publication Data
US 2022/0283139 A1    Sep. 8, 2022

(30) Foreign Application Priority Data
Aug. 28, 2019   (EP) .................................... 19194104

(51) Int. Cl.
*G01N 33/34* (2006.01)
*D21F 7/00* (2006.01)
(Continued)

(52) U.S. Cl.
CPC ............... *G01N 33/34* (2013.01); *D21F 7/00* (2013.01); *D21J 1/00* (2013.01); *G06N 20/00* (2019.01)

(58) Field of Classification Search
CPC .. G01N 33/346; G01N 21/23; G01N 21/3559; G01N 21/3581; G01N 21/86;
(Continued)

(56) References Cited

U.S. PATENT DOCUMENTS 5,282,131 A   1/1994   Rudd
5,942,689 A   8/1999   Bonissone et al.
(Continued)

FOREIGN PATENT DOCUMENTS

EP   2781911 A1   9/2014
WO   03074784 A1   9/2003

OTHER PUBLICATIONS

Huang, S.; Tang, J.; Dai, J.; Wang, Y. Signal Status Recognition Based on 1DCNN and Its Feature Extraction Mechanism Analysis. Sensors 2019, 19, 2018. https://doi.org/10.3390/s19092018 (Year: 2018).*

(Continued)

*Primary Examiner* — Son T Le
*Assistant Examiner* — Brian Butler Geiss
(74) *Attorney, Agent, or Firm* — Wolter Van Dyke Davis, PLLC

(57) ABSTRACT

A computer-implemented method for estimating at least one quality parameter of paperboard produced in a paperboard production subprocess of a paperboard processing pipeline by a data-driven module having a preprocessing module and a machine-learning module. Sensor data is acquired along the processing pipeline. Features are extracted from the sensor data by the preprocessing module. The machine-learning module is trained to reproduce target quality values
(Continued)

from historical features. After training, the machine-learning module processes real-time features and estimates at least one quality parameter. A system implements the computer-implemented method and to a paperboard production machine includes such a system.

15 Claims, 2 Drawing Sheets

(51) Int. Cl.
*D21J 1/00* (2006.01)
*G06N 20/00* (2019.01)

(58) Field of Classification Search
CPC ..... G01N 2291/0237; G01N 2291/044; G01N 29/07; G01N 29/4481
See application file for complete search history.

(56) References Cited

U.S. PATENT DOCUMENTS

| | | | |
|---|---|---|---|
| 6,187,145 | B1 | 2/2001 | Furumoto et al. |
| 2009/0120190 | A1* | 5/2009 | Pettersson ............. G01N 29/48 73/598 |
| 2014/0277674 | A1 | 9/2014 | Van Mechelen et al. |
| 2021/0042570 | A1* | 2/2021 | Iskandar ............. G06F 11/3075 |

OTHER PUBLICATIONS

Sha Lizheng, Gao Jun and Wang Jianhua, "Pulp concentration control by PID with BP neural network in the production of light weight cardboard," 2010 IEEE 11th International Conference on Computer-Aided Industrial Design & Conceptual Design 1, Yiwu, 2010, pp. 1217-1220, doi: 10.1109/CAIDCD.2010.5681989 (Year: 2010).*
A. Skoglund et al: "Comparison Between Linear and Nonlinear Prediction Models for Monitoring of a Paperboard Machine", Chemical Engineering and Technology, vol. 25. No. 2. Feb. 1, 2002 (Feb. 1, 2002), p. 197, XP055664634.
PCT International Search Report and Written Opinion of International Searching Authority mailed Nov. 26, 2020 corresponding to PCT International Application No. PCT/EP2020/073139 filed Aug. 19, 2020.

* cited by examiner

METHOD, SYSTEM AND PAPERBOARD PRODUCTION MACHINE FOR ESTIMATING PAPERBOARD QUALITY PARAMETERS

CROSS REFERENCE TO RELATED APPLICATIONS

This application is the US National Stage of International Application No. PCT/EP2020/073139 filed 19 Aug. 2020, and claims the benefit thereof. The International Application claims the benefit of European Application No. EP19194104 filed 28 Aug. 2019. All of the applications are incorporated by reference herein in their entirety.

FIELD OF INVENTION

The invention is related to a method and to a system for estimating paperboard quality parameters. The invention is also related to a paperboard production machine implementing such method for estimating paperboard quality parameters.

BACKGROUND OF INVENTION

Paperboard is continuously produced in a processing pipeline comprising a plurality of processing steps, for example mixing incoming pulp, refining pulp, chemically treating pulp and processing pulp by a paperboard machine. The produced paperboard is winded on large reels, wherein one reel may contain paperboard of about 40 kilometres length and about seven metres width. The processing steps may be controlled by settings and/or described by parameters which affect the quality of the produced paperboard. Furthermore, environmental parameters such as temperature or humidity may affect the quality. Changes of processing and environmental parameters may affect the quality in a delayed and non-linear way.

Various quality parameters that describe the quality of paperboard are known from the state of the art.

As an example, a quality parameter denoted as Z-strength is known that describes the strength of a paperboard along its surface normal. As a further example, a quality parameter denoted as Scott bond is known that describes the in-plane strength of a paperboard.

Valid ranges may be specified for one or more of such quality parameters. Paperboard with quality parameters outside this specification is either to be downgraded or to be dumped.

In order to determine these quality parameters, according to the state of the art samples are taken manually from a paperboard reel across its width. Such samples are prepared and analysed manually or semi-manually in a laboratory. Due to the high speed of the paperboard machine, samples cannot be taken while paperboard is winded on the reel. Thus, samples can usually be taken about every 45 minutes. The manual or semi-manual analysis takes about further 20 minutes. Therefore, the status and/or the trend of quality parameters are unknown for a longer period, which poses the risk of a substantial scrap rate in paperboard production.

There is thus a need for an improved estimation of paperboard quality.

SUMMARY OF INVENTION

It is an object of the present invention to provide an improved method for estimating at least one quality parameter of paperboard produced in a paperboard production subprocess of a processing pipeline. This object is achieved by a computer-implemented method according to the claims.

It is a further object of the present invention to provide an improved system for estimating at least one quality parameter of paperboard produced in a paperboard production subprocess of a processing pipeline. This object is achieved by a system according to the claims.

It is yet a further object of the present invention to provide a paperboard production machine implementing an improved method for estimating at least one quality parameter of the paperboard produced. This object is achieved by a paperboard production machine according to the claims.

Exemplary embodiments of the invention are given in the dependent claims.

According to a first aspect of the invention, a computer-implemented method is designed for estimating at least one quality parameter of paperboard that is produced in a paperboard production subprocess which is a subprocess of a paperboard processing pipeline. The paperboard processing pipeline is implemented by a data-driven module that comprises a preprocessing module and a machine learning module and comprises at least one processing step implemented by a processing unit or machine. The computer-implemented method comprises the following steps:

The computer-implemented method comprises a step, wherein sensor data is acquired from at least one processing step of the processing pipeline and transferred to a data repository. The data repository is designed to store sensor data persistently. Advantageously, the data repository is accessible via an internet protocol (IP). Most advantageously, the data repository is formed as a cloud storage.

The computer-implemented method comprises a further step, wherein at least one historical feature is determined by the preprocessing module by at least partially evaluating historical sensor data. Such historical sensor data was acquired during at least one previously produced batch of paperboard and is retrieved from the data repository.

The computer-implemented method comprises a further step, wherein a machine-learning module is trained to reproduce from the at least one historical feature a target value of at least one quality parameter. This target value is determined for a previously produced batch of paperboard corresponding to the historical sensor data from which the historical feature was determined. As an example, the target value may have been determined by measurements in a laboratory and transferred to the data repository, where it was associated with the respective historical sensor data.

The computer-implemented method comprises a further step, wherein least one real-time feature is determined by the preprocessing module from a stream of current sensor data being acquired from a currently produced batch of paperboard and retrieved from the data repository.

The computer-implemented method comprises a further step, wherein an estimate for at least one quality parameter of the produced paperboard is determined from the at least one real-time feature by the trained machine-learning module and provided as output value of the data-driven module.

It is an advantage of this method that a quality parameter of the produced paperboard may be estimated continuously during the production and with a lower latency relative to known methods. Thereby, the paperboard production subprocess may be controlled more precisely and a target value or range for a targeted quality parameter of the produced paperboard is met more reliably. Thus, costs associated with dumped or downgraded paperboard may be reduced and the efficiency of the paperboard production may be improved.

It is a further advantage of the method that sensor data is stored centrally and independent of the physical location of machines performing processing steps in the paperboard production. Thereby, a more comprehensive data analysis is enabled that improves the prognostic accuracy of the paperboard quality estimation and helps to detect failures and flaws along the paperboard production subprocess. Furthermore, the risk of data loss and data inconsistencies is reduced.

According to an embodiment of the invention, the historical sensor data is split into a plurality of intervals, advantageously into 10000 intervals or more. Episodes of historical sensor data that are associated with error messages or inconsistencies that were logged and stored in the data repository are omitted.

It is an advantage of this embodiment that a higher number of training samples is provided for the training of the machine-learning module, wherein a training sample comprises a feature derived from the split historical sensor data and a target quality value associated with that split historical sensor data. Thereby and by removing unreliable episodes, the machine-learning module is trained such that it provides a more precise and more reliable estimate of the quality parameter on streaming current sensor data.

According to an embodiment of the invention, a delay group is determined for a processing step. Said delay group defines a minimum latency time with which a parameter change in that processing step takes effect on affect the outcome of the production subprocess. Current sensor data that is acquired within this latency time of the respective delay group, counted backwards from the current production time stamp, is excluded from evaluation by the data-driven module.

It is an advantage of this embodiment that sensor data with no potential prognostic value for the estimation of a quality parameter, being effectively noise, is removed from the training as well as from the operational prediction of the machine-learning module. Thereby, the machine-learning module may be trained more efficiently and the estimation accuracy and reliability may be improved.

According to an embodiment of the invention, at least one feature comprises at least one time series. Said time series describes the variation of at least one parameter of the sensor data along discrete time intervals or time windows. The machine-learning module performs a one-dimensional (1D) convolution of the at least one time series along the time axis.

It is an advantage of this embodiment that in the training of the machine-learning module parameters of the 1D convolution, which forms a filter operating on the respective time series, are adjusted such as to optimise the reproduction of the target quality value. Thereby, features with a particular predictive value are extracted from the respective time series. Thereby, the machine-learning module may be trained more efficiently and the estimation accuracy and reliability may be improved.

According to an embodiment of the invention, for a discrete time window or time interval at least one statistical parameter, advantageously a mean value and/or a standard deviation value, is determined such as to form a sample value of the at least one time series.

It is an advantage of this embodiment that a statistical parameter is a more reliable characterisation of a process status during such a time window than the plurality of individually sampled values that it is determined from. Thereby, the machine-learning module may be trained more efficiently and the estimation accuracy and reliability may be improved.

According to an embodiment of the invention, the validity and/or the consistency of current sensor data is evaluated and optionally logged in the data repository by the preprocessing module. This enables the preprocessing module to determine invalid or unreliable episodes of the current sensor data and remove those from the estimation of the quality parameter. Thereby, the machine-learning module may be trained more efficiently and the estimation accuracy and reliability may be improved.

According to an embodiment of the invention, one quality parameter estimated by the data-driven module is a Z-strength of the paperboard. The Z-strength is an established parameter of particular relevance for the grading of the produced paperboard. As an advantage, this embodiment reduces costs associated with dumped or downgraded paperboard and improves the efficiency of the paperboard production.

According to an embodiment of the invention, one quality parameter estimated by the data-driven module is a Scott bond of the paperboard. The Scott bond is an established parameter of particular relevance for the grading of the produced paperboard. As an advantage, this embodiment reduces costs associated with dumped or downgraded paperboard and improves the efficiency of the paperboard production.

According to an embodiment of the invention, at least one range for a quality parameter is provided as additional input to the data-driven module, wherein for each range a probability value for the respective quality parameter to fall within the respective range is determined as an output value. For a scalar quality parameter, a range can be formed as a closed, an open or a half-open interval.

As an advantage, this embodiment enables a more detailed estimation of a quality parameter that better reflects its stochastic nature.

According to an embodiment of the invention, for one or more of the probability values determined by the data-driven module for a range of a quality parameter, each probability value is compared with a probability limit assigned to the respective range and the respective quality parameter, resulting in one Boolean comparison value per range and quality parameter. A predetermined Boolean expression depending on the at least one Boolean comparison value is evaluated, wherein an alarm is triggered, when the predetermined Boolean expression returns logical true.

It is an advantage of this embodiment that a status of the paperboard production subprocess, in which a quality value is potentially compromised, can be detected automatically, objectively and with a particularly low latency.

According to an embodiment of the invention, for at least one quality parameter a first range is a set of invalid values lower than a lower valid limit, a second range is a set of valid values between the lower valid limit and an upper valid limit and a third range is a set of invalid values higher than the upper valid limit, wherein an alarm is triggered, when the probability value associated with the first range exceeds a predetermined first probability limit or when the probability value associated with the second range falls below a predetermined second probability limit or when the probability value associated with the third range exceeds a predetermined third probability limit.

For the sake of clarity and better understanding, an example is provided for this embodiment:

As an example, for a scalar parameter q a first range $r_1=\{q|q<q_l\}$ is determined as open interval of values below a lower limit $q_l$. A second range $r_2=\{q|q_l\leq q\leq q_u\}$ is determined as a closed interval between the lower limit $q_l$ and an upper limit $q_u$. A third range $r_3=\{q|q>q_u\}$ is determined as open interval of values above the upper limit $q_u$.

The data-driven module is designed, in particularity trained, such that it provides a first output corresponding to a first probability value for the quality parameter to be in the first interval, $p_1=P[q\in r_1]$. A second and a third output correspond to the probability value for the quality parameter in the second and third interval, respectively: $p_2=P[q\in r_2]$, $p_3=P[q\in r_3]$.

A conditional predetermined Boolean expression can then be formed such as $(p_1>\theta_1)$ OR $(p_2<\theta_2)$ OR $(p_3>\theta_3)$ wherein $\theta_1$, $\theta_2$, $\theta_3$ denote probability limits for the first to third probability value $p_1$, $p_2$, $p_3$ respectively, and "OR" denotes a logical (Boolean) or-expression. An alarm is triggered, when said predetermined Boolean expression is evaluated as logical (Boolean) true.

It is an advantage of this embodiment that a status of the paperboard production subprocess, in which a quality value is potentially compromised, can be detected particularly easy.

According to a second aspect of the invention, a system comprises at least one sensor, a data repository and a computing means.

The at least one sensor is designed to acquire sensor data in a processing step of a processing pipeline comprising a paperboard production subprocess. As an example, a sensor may be designed to measure a temperature of pulp, an environmental temperature, an environmental humidity or the concentration of one or more components of pulp.

The data repository is designed to receive and persistently store sensor data from the at least one sensor and to transfer sensor data towards the computing means.

The computing means comprises (i.e. implements) a computer-implemented method according to the first aspect of the invention.

By means of said system, the advantages related to a computer-implemented method for estimating at least one quality parameter of paperboard produced in a paperboard production subprocess can be reached as explained before. As a further advantage, sensors, data storage for forming a data repository and computing means for implementing such a method are readily available.

According to an embodiment of the invention, the data storage is formed as a cloud storage that can be accessed by an internet protocol (IP) based communication protocol stack. Cloud storage provides many advantages such as relative inexpensiveness, good scalability, good reliability and availability. As a further advantage, the cloud storage is decoupled from the paperboard processing pipeline and its physical components. Thereby, a more flexible and versatile data analysis is enabled that allows an improved accuracy and reliability of the estimation of the at least one quality parameter. As an example, sensor data of more than one physical instance of a paperboard processing pipeline can be merged in a data repository formed as cloud storage. Thus, a machine-learning module may be trained such that it is less prone to random irregularities along one specific paperboard processing pipeline.

According to an embodiment of the invention, the system comprises a signalling means which is designed for being triggered by the computing means. The signalling means is designed to indicate the need of manual interaction with the paperboard production subprocess when being triggered. This embodiment enables an immediate response to a process status that potentially compromises a quality parameter of the produced paperboard. Thereby, the risk and/or amount of paperboard to be dumped or downgraded is reduced.

According to a third aspect of the invention, a paperboard production machine which is designed to produce paperboard or a semi-product of paperboard along a paperboard production subprocess comprises a system according to the second aspect of the invention.

By means of said system, the advantages related to a computer-implemented method for estimating at least one quality parameter of paperboard produced in a paperboard production subprocess can be reached as explained before. In particularity, a paperboard production machine according to the invention provides a better efficiency and a better and more reliable quality of the produced paper.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION OF INVENTION

Corresponding parts are marked with the same reference symbols in all figures.

Figure 1:
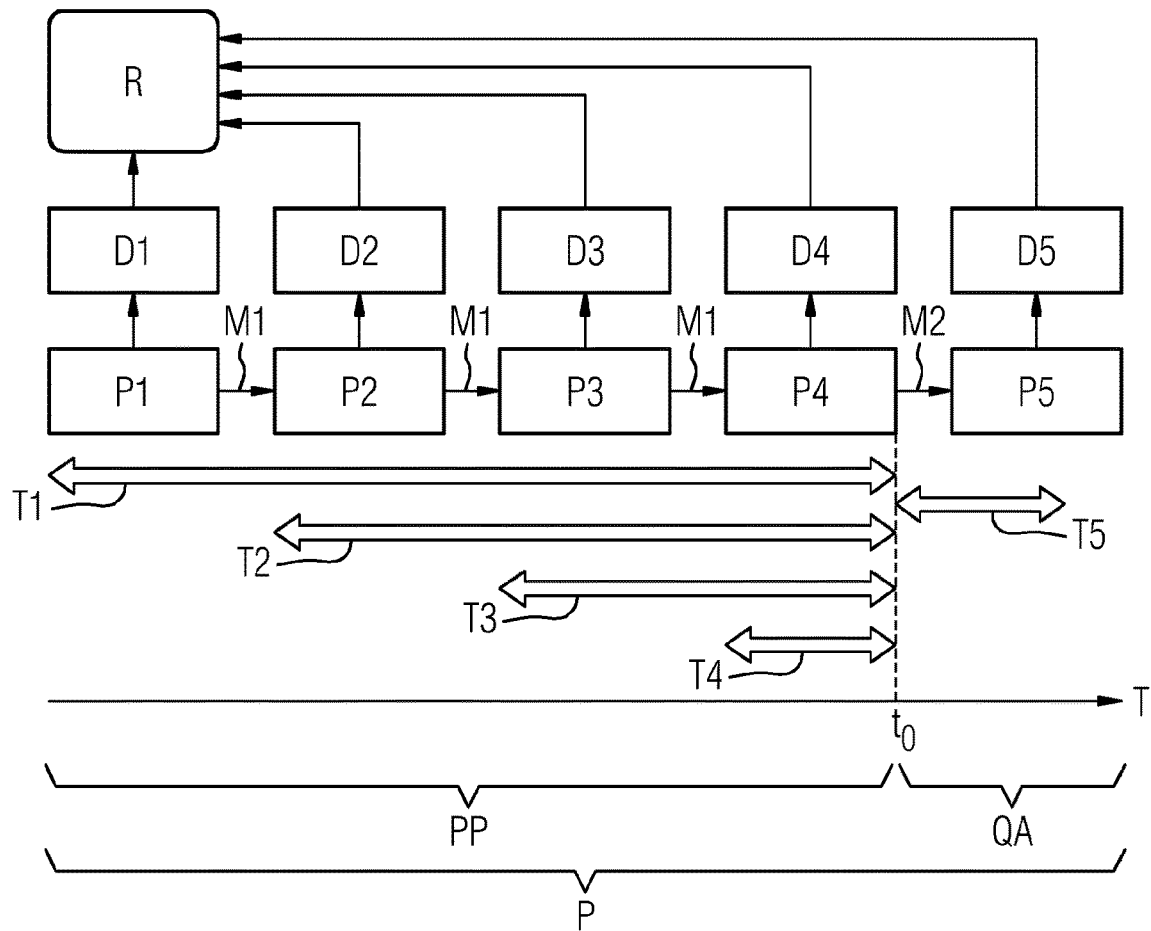
FIG. 1 schematically shows sensor data acquisition along a paper processing pipeline, FIG. 2 schematically shows a data-driven model for paper quality parameter estimation, FIG. 3 schematically shows the extraction of statistical features from sensor data, FIG. 4 schematically shows a machine learning model for paper quality parameter estimation and FIG. 5 schematically shows a classification model for classifying a paper quality parameter.

FIG. 1 schematically shows a processing pipeline P for paper production, wherein material M1, M2 is sequentially processed through a plurality of processing steps P1 to P5.

By way of example, a first processing step P1 is constituted by preparing incoming pulp. A subsequent second processing step P2 is constituted by refining pulp. A subsequent third processing step P3 is constituted by chemically treating the refined pulp. A subsequent fourth step P4 is constituted by setting parameters of a paperboard machine. A subsequent fifth processing step P5 is constituted by quality measurements in a laboratory. Thus, in this example, the first through fourth processing steps P1 to P4 form a production subprocess PP, whereas the fifth processing step P5 forms a quality assurance subprocess QA Along the first through the fourth processing step P1 to P4, material is passed as wet pulp M1. Material for the fifth processing step P5 is passed from the paperboard machine as paperboard samples M2. For example, a paperboard sample M2 is cut from the end of a reel on which continuously produced paperboard is winded on and is manually passed to a remotely located laboratory.

Different processing steps P1 to P5 may be performed by physically different processing units or machines at physically different locations. However, it is also possible that a plurality of processing steps P1 to P5 is performed by a single processing unit or machine.

Irrespective of its physical implementation and location, each of the processing steps P1 to P5 is associated with and characterized by specific current sensor data D1 to D5, respectively, and can thus be seen as a sensor data source.

As an example, current sensor data D5 associated with the fifth processing step P5 can be provided as Z-strength and Scott-bond measurement values for a respective paperboard sample M2, i.e. a time-discrete, two-dimensional value vector sampled with a frequency of about once per hour. Other paper quality parameters may be provided additionally or alternatively, such as humidity or grammage.

As a further example, current sensor data D1 associated with the first processing step P1 can be provided as a categorical or numerical value describing the quality of the incoming pulp.

Further current sensor data D1 to D5 may be related to parameters of the respective processing step P1 to P4, such as settings of the pulp refining process or as parameters of the chemical preparation of the pulp or as settings of a specific paper production machine designed to perform one or more of the processing steps P1 to P4.

According to the invention, current sensor data D1 to D5 of a plurality of processing steps P1 to P5 is transferred to a central sensor data repository R. Advantageously, current sensor data D1 to D5 of all processing steps P1 to P5 is transferred to the central sensor data repository R.

In an embodiment, the data repository R is formed as cloud storage such as, for example, a SIEMENS MindSphere storage. As an advantage, such an embodiment is independent of a dedicated data network infrastructure such as a proprietary field bus. The data repository R may thus be retained fully functional even during or after a physical relocation of a machine or processing unit. Furthermore, it is possible to merge sensor data for the entire processing pipeline P in a single location irrespective of the physical location of the individual processing steps P1 to P5. For example, the laboratory for determining quality parameters of the paperboard samples M2 in the fifth processing step P5 may be located in a different building than the paperboard machine performing the fourth processing step P4.

Furthermore, sensor data is available independent of the life cycle of a specific machine or even a model of a machine, thereby providing advantages with regard to availability, consistency and safety of recorded sensor data D1 to D5.

From the sequential order of the processing steps P1 to P5 along a time axis T, delay groups T1 to T5 may be derived, wherein each processing step P1 to P5 is associated with one delay group T1 to T5.

A delay group T1 to T5 determines a time shift of the acquisition of current sensor data D1 to D5 relative to a production timestamp t0 defining the completion of a certain production batch. This time shift is discretized along the time axis T. As an example, such a time shift may be defined as a multiple of a ground time interval of 15 minutes.

More specifically, delay groups T1 to T4 assigned to the processing steps P1 to P4 of the production subprocess PP are determined as the time span or latency that in the minimum is required for a change in such processing step P1 to P4 (be it a variation of a processing parameter, a machine setting or a parameter of wet pulp material M1 at the input of said processing step P1 to P4) to effect any of the observed quality parameters of the produced paper batch.

Current sensor data D1 to D4 derived from a processing step P1 to P4 of the production subprocess PP is eliminated for sensor data processing when it was acquired within the delay group T1 to T4 associated with the respective processing step P1 to P4.

According to the invention, the same delay group T1 to T5 is applied to all current sensor data D1 to D5 derived from the same processing step P1 to P5.

For example, a pulp refining process P2 may be assigned a delay group $T2=45$ minutes. Said pulp refining process P2 may be characterized by refiner settings, a wet pulp temperature and an environment temperature and possibly further parameters, all of which are acquired and transferred as sensor data D2 to the data repository R. Values of any such sensor data D2 taken at a time tx will only then be considered for prediction of some quality parameter, if they lag more than the latency of the associated delay group T2, i.e.

$tx-t0>T2$.

A delay group T5 assigned to a processing step P5 of the quality assurance subprocess QA defines the delay of quality measurements (made available as sensor data D5) relative to the production time stamp t0 and is used for aligning (in time) this sensor data D5 relative to the production time stamp to.

Figure 2:
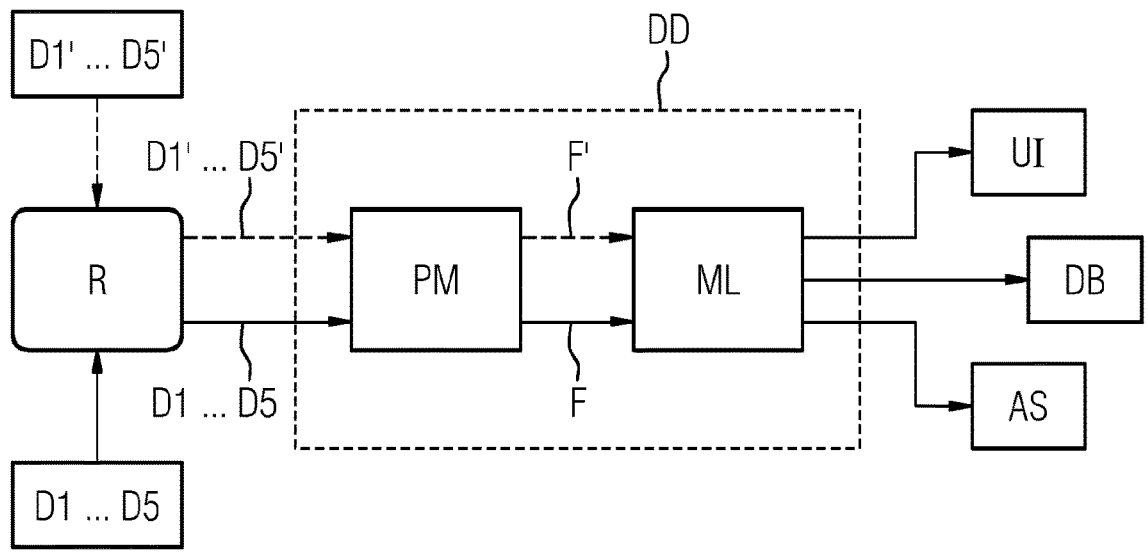

FIG. 2 schematically shows the data flow through a data-driven model DD for the estimation of at least one paper quality parameter such as Z-strength and/or Scott-bond. The data-driven model DD comprises a preprocessing module PM and a machine learning module ML. The data-driven model DD is driven by data retrieved from the central data repository R comprising current sensor data D1 to D5 from the current paper production process but also historical sensor data D1' to D5' that was acquired and passed to the data repository R during the production of previous batches.

Sensor data D1 to D5 and historical sensor data D1' to D5' is passed to the preprocessing module PM, where features F, F', for instance statistical parameters, are extracted. Real-time features F are extracted from current sensor data D1 to D5 that is acquired from the current paper production process. Historical features F' are extracted from historical sensor data D1' to D5' that was previously acquired in the production of preceding batches.

The preprocessing module PM checks the consistency and validity of the sensor data D1 to D5, D1' to D5'. It analyses whether valid data is received from all incorporated data sources, in particularity from all machines and/or processing units associated with a processing step P1 to P5 along the processing pipeline P. As an example, the preprocessing module PM explicitly searches for missing timestamps or missing sensors along the sensor data D1 to D5, D1' to D5'. Furthermore, the preprocessing module PM may verify if previously specified events along the processing pipeline P, such as a shut-down of the entire production subprocess PP or parts thereof appear correctly. Each specific consistency check logs an error when it fails.

The extraction of features F, F' by the preprocessing module PM is explained in more detail using FIG. 3 later on.

Features F, F' are passed to the machine-learning model ML that estimates one or more paper quality parameter from these features F, F'. In an embodiment, the machine-learning model ML may also be formed, in particularity be trained, to detect from the real-time features F a violation of a specification of a certain parameter and to trigger an alarm. As an example, an alarm may be triggered when a parameter estimated by the machine-learning module leaves a predetermined range. Details of such parameter classification are explained using FIG. 5 later on.

The machine-learning model ML may operate in a training or retraining mode, in which it is adapted using historical features F'. Optionally, in the training or retraining mode, the machine-learning model ML may additionally, for example by means of unsupervised learning, be adapted using real-time features F.

The machine-learning model ML may further operate in a real-time estimation (or prediction) mode, in which it determines, predicts and/or classifies one or more quality parameters based on real-time features F.

The machine-learning model ML is designed to interface with a User Interface UI of a software product and/or with a database DB designed to store data persistently and/or with an alarm system AS designed to issue a signal indicating a need for manual intervention in the processing pipeline.

Figure 3:
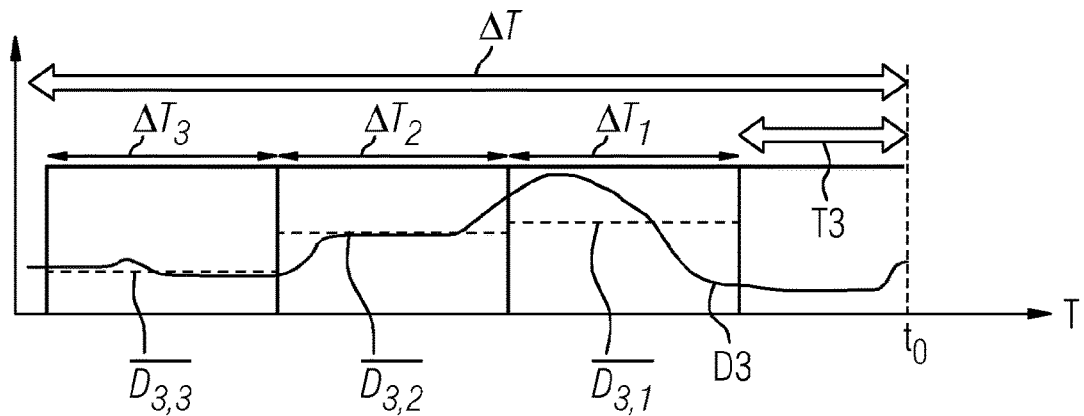

FIG. 3 schematically and exemplary illustrates the extraction of features F of sensor data D3 associated with a group delay T3 performed by the preprocessing module PM, which is not explicitly shown in FIG. 3.

The sensor data D3 is acquired along a data history ΔT. Sensor data D3 that is more recent than the associated group delay T3 is not considered for preprocessing, as it is a priori known that this cannot possibly affect (or predict) quality parameters observed at the production time stamp to.

The remaining data history ΔT is divided into time windows $\Delta T_i$, i=1, 2, 3, . . . . One or more statistical parameters is or are determined for each of the time windows $\Delta T_1$, $\Delta T_2$, $\Delta T_3$. By way of example only, mean values $\overline{D_{3,1}}$, $\overline{D_{3,2}}$, $\overline{D_{3,3}}$ are schematically illustrated in FIG. 3 that were derived from the time course of the sensor data D3 in the respective time windows $\Delta T_1$, $\Delta T_2$, $\Delta T_3$. Other statistical parameters may be derived per time window $\Delta T_1$, $\Delta T_2$, $\Delta T_3$, additionally or alternatively, including yet not restricted to standard deviation, higher order moments or, for multivariate sensor data D3, covariances.

Instead of current sensor data D3, the preprocessing module PM may also process historical sensor data D1' to D5' (not explicitly shown in FIG. 3). The preprocessing module PM distinguishes between processing current sensor data D3, which is provided as streaming data by the data repository R, and processing historical sensor data D1' to D5'.

For the case of streaming current sensor data D3, one single sample of a real-time feature F is generated, which may be formed as a feature vector comprising a plurality of scalar, e.g. statistical parameters. Together with the real-time feature F derived from the streaming current sensor data D3, specific errors detected by the preprocessing module PM such as inconsistencies or events detected along the processing pipeline P such as shut-downs may be retrieved from the data repository R and passed to the machine-learning module ML.

For the case of historical sensor data D1' to D5', such data is split into a plurality of intervals to create a high number of samples of a historical feature F' being used for training the machine-learning model ML. As an example, historical sensor data D1' to D5' may be split into 10000 intervals which may be disjunct or partly overlapping. When splitting historical sensor data D1' to D5', episodes that comprise errors such as inconsistencies or irregular events such as shut-downs or partial shut-downs of the processing pipeline may be dropped from the generated intervals.

Also, along with the historical sensor data D1' to D5' ground-truth data describing the actually verified quality parameter is retrieved from the data repository R and passed on to the machine learning module ML, thus enabling supervised learning.

A feature F, F' may be formed by a single statistical parameter or by a plurality of statistical parameters. By statistical parameters, the dimensionality of observed sensor data D1 to D5, D1' to D5' may be reduced. The robustness of a statistical data representation may be improved as it is less sensitive to outliers. Real-time features F are extracted from current sensor data D1 to D5. Historical features F' are extracted from historical sensor data D1' to D5'. All extracted features F, F' are converted into a format that is compatible to the input of the machine-learning module ML.

Figure 4:
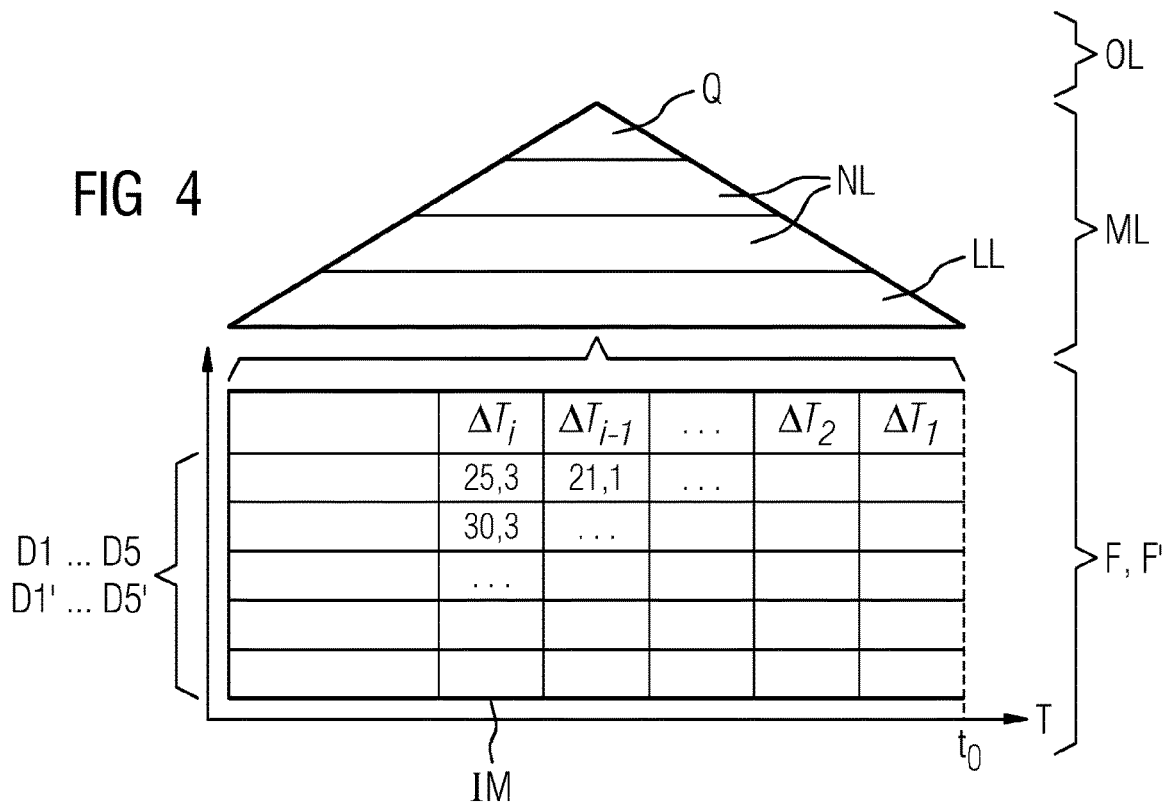

FIG. 4 explains the machine-learning model ML in more detail. The machine learning model ML is a mathematical model which learns from processing historical sensor data D1' to D5' in a supervised learning phase. After the supervised learning phase, the trained machine-learning model ML is used to estimate at least one product quality parameter it was trained on.

The supervised learning is performed by minimizing a cost function which must be defined so that it exhibits a minimum when the deviation between the estimated and the measured product quality parameter, usually defined by a distance metric such as a Euclidian or Manhattan distance, is vanishing or minimized. The minimization of the cost function is done by applying stochastic gradient-descent, a class of methods which adapt the stochastically initialized parameters of the model iteratively until a certain accuracy is reached. Stochastic gradient-descent methods are known from the state of the art.

As an example, the machine-learning model ML may be formed as a multi-layered artificial neural network comprising at least one one-dimensional (1D) convolutional layer CL as input layer and a plurality of neuron layers NL that are densely connected. The layers CL, NL are arranged in a stack of layers with the first (lowest) layer being the input convolutional layer CL and the last (uppermost) layer being an output neuron layer OL. Neighbouring neuron layers NL may be densely connected such that each of the neurons in the respective upper neuron layer NL receives input from all of the neurons in the respective lower neuron layer NL. Connections between neurons are associated with weights that constitute free parameters of the artificial neural network ML.

The uppermost output neuron layer OL comprises at least one neuron that generates a model output value corresponding to a paper quality parameter value.

In the real-time estimation (or prediction) mode, the at least one model output value forms a prediction or an estimate of a paper quality parameter Q.

In the training or retraining mode, the at least one model output value is compared with at least one ground-truth parameter value by means of a distance metric, thereby determining an error value. The free parameters of the artificial neural network ML are adapted such that, in a stochastic sense, said error value is minimised. Supervised learning methods for adapting free parameters of an artificial neural network ML are known from the state of the art.

On the convolutional layer CL at its input side, the artificial neural network ML is fed with features F, F' extracted by the preprocessing module PM. These features F, F' may be formed as an input matrix IM, wherein one horizontal row of the input matrix IM corresponds to a specific time-varying parameter of sensor data D1 to D5, D1' to D5', and wherein one vertical row of the input matrix IM corresponds to a certain time window $\Delta T_i$, i=1, 2, 3, . . . . In other words, along its horizontal dimension, the input matrix IM reflects variation over time and along its vertical dimension, the input matrix captures the different signals measured in the processing pipeline P.

Within the 1D convolutional layer CL, the convolution is applied along the time axis T, i.e. along the horizontal dimension of the input matrix IM. The 1D convolutional layer CL provides a set of filters for each of the rows of the input matrix IM.

As an example, a first convolutional filter may be provided for the first row of the input matrix IM, which holds features F, F' derived from a first sensor parameter being part of the first sensor data D1. Said first convolutional filter may be configured to access values from three consecutive time windows $\Delta T_{i-1}, \Delta T_i, \Delta T_{i+1}$ which are shifted along the time axis T, i.e. along the row (e.g., from $\Delta T_{i-1}, \Delta T_i, \Delta T_{i+1}$ first to $\Delta T_i, \Delta T_{i+1}, \Delta T_{i+2}$, then to $\Delta T_{i+1}, \Delta T_{i+2}, \Delta T_{i+3}$ etc.).

In analogy to the first convolutional filter, further convolutional filters may be provided for the same first row of the input matrix IM.

In the same way, convolutional filters are provided within the 1D convolutional layer CL for every row of the input matrix IM, wherein the support of every convolutional filter need not be restricted to one row of the input matrix IM.

In the training/retraining mode, the behaviour of these convolutional filters is adapted according to the error criterion to be minimized. As an example, filter coefficients of a convolutional filter formed as a finite impulse response (FIR) filter are adapted according to the error criterion. For this, a plurality of instances of the input matrix IM is presented to the artificial neural network ML, wherein for each instance the at least one output value is calculated at the output layer OL and an error value is determined according to the chosen distance metric.

The initial parameters of the artificial neural network ML, including the parameters of the convolutional filters in its 1D convolutional layer, are initialised randomly. The same result, i.e. an identical performance of the trained artificial neural network ML, can thus in general not be guaranteed for multiple training/retraining runs according to the state of the art.

To improve stability and robustness of the training result, a plurality of convolutional filters is used, of which a certain proportion is switched off for a certain number of training cycles. Such regularisation methods are known as dropout from the state of the art. Thereby, redundancy is retained within the plurality of trained convolutional filters. The training result is thus less sensitive to the random initialisation and less prone to local minima of the error criterion.

As an example, for a set of about 70 different sensors providing parameters (time series), about 100 convolutional filters may be used.

In an embodiment, a set of instances of the input matrix IM may be dichotomised into training data and into evaluation data. The training data and the evaluation data may also be chosen to overlap slightly. As an example, the training data may be derived from historical sensor data D1' to D5' from January 2017 to April 2019, while the evaluation data may be derived from historical sensor data D1' to D5' from February 2019 to April 2019, so that only a minor subset of training data is part of the evaluation data. As an advantage, the most recent data is then used for adapting the artificial neural network ML, thereby improving its performance on the current processing pipeline P.

Figure 5:
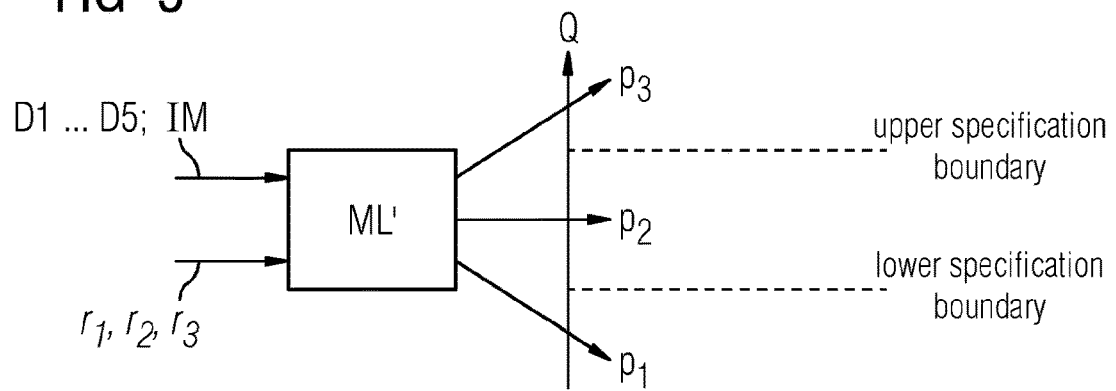

A machine-learning model ML' can also be used for a classification of current sensor data D1 to D5 as schematically illustrated in FIG. 5. This machine-learning model ML' can be implemented as an own dedicated machine-learning model or as an extension of the artificial neural network ML according to FIG. 4.

At its input, the machine-learning model ML' can be provided with an input matrix IM as shown in FIG. 4. Alternatively or additionally, the machine-learning model ML' can be provided with a paper quality parameter Q as estimated by the artificial neural network ML according to FIG. 4, i.e. one or more output values of the output layer OL.

Furthermore, the machine-learning model ML' is provided with specification boundary parameters that indicate at least one range $r_1, r_2, r_3$ for the respective paper quality parameter Q. As an example, for a scalar paper quality parameter Q, an upper and a lower specification boundary is provided, when the scalar paper quality parameter Q is considered valid in between the lower and the upper specification boundary.

For historical input data, it is known whether the corresponding paper quality parameter Q is inside, beyond or below the specified range $r_1, r_2, r_3$. Thus, the machine-learning model ML' can be trained by supervised learning in the same way as previously described for the artificial neural network ML.

According to this aspect of the invention, the machine-learning model ML' after the training determines a first, a second and a third probability value p1, p2, p3. The first probability value p1 indicates the probability that the paper quality parameter Q falls below the lower specification boundary, i.e. within the first valid range $r_1$. The second probability value p2 indicates the probability that the paper quality parameter Q is inside the second specification range $r_2$, i.e. is greater than or equal to the lower specification boundary and is lower than or equal to the upper specification boundary. The third probability value p3 indicates the probability that the paper quality parameter Q exceeds the upper specification boundary, i.e. is within the third range $r_3$.

Depending on the probability values p1, p2, p3, an alarm will be triggered when the paper quality parameter Q is expected to be outside the specified valid range. As an example, an alarm will be triggered if at least one of the following conditions is met: the first probability value p1 exceeds 0.1 OR the third probability value p3 exceeds 0.1 OR the second probability value p2 falls below 0.85.

As an advantage, such an alarm enables checking or possibly adjusting the production subprocess PP such that the specified quality parameter range $r_2$ is reached again even if final quality data from the laboratory based on paper board samples M2 is not yet available. Thereby, the produced amount of paper board that fails to fulfil the specified quality criteria may be reduced.

REFERENCE SIGNS

AS alarm system
CL 1D convolutional layer
D1 to D5 real-time sensor data, sensor data
D1' to D5' historical sensor data, sensor data
$\overline{D_{3,1}}, \overline{D_{3,2}}, \overline{D_{3,3}}$ mean value
DB database
DD data-driven model
F real-time feature
F' historical feature IM input matrix
M1 wet pulp, material
M2 paperboard samples, material
ML machine-learning module, artificial neural network
ML' machine-learning module
NL neuron layer
OL output layer
P processing pipeline
PM preprocessing module
PP production subprocess
P1 to P5 processing step
p1, p2, p3 first, second, third probability value
Q paper quality parameter
QA quality assurance subprocess
R data repository
$r_1, r_2, r_3$ range
T time axis
t0 production time stamp
T1 to T5 delay group
ΔT data history
$\Delta T_i$, i=1, 2, 3, . . . time window
UI user interface

The invention claimed is:

1. A computer-implemented method for estimating at least one quality parameter of paperboard produced in a paperboard production subprocess of a paperboard processing pipeline during the production by a data-driven module comprising a preprocessing module and a machine-learning module, the method comprising:
acquiring sensor data from at least one processing step of the processing pipeline and transferring the sensor data to a data repository,
determining at least one historical feature by the preprocessing module by at least partially evaluating historical sensor data that was acquired during at least one previously produced batch of paperboard and retrieved from the data repository,
training the machine-learning module to reproduce from the at least one historical feature a target value of the at least one quality parameter, wherein the target value is determined for a previously produced batch of paperboard corresponding to the historical sensor data from which the historical feature was determined,
determining at least one real-time feature by the preprocessing module from a stream of current sensor data being acquired from a currently produced batch of paperboard and retrieved from the data repository,
determining an estimate for the at least one quality parameter from the at least one real-time feature by the trained machine-learning module and providing the estimate as an output value,
adjusting the paperboard production subprocess in response to the output value not being within a predetermined range,
wherein at least one range for the at least one quality parameter is provided as additional input to the data-driven module, wherein for each range a probability value for the respective quality parameter to fall within the respective range is determined as an output value,
wherein for one or more of the probability values determined by the data-driven module for the range of the at least one quality parameter, each probability value is compared with a probability limit assigned to the respective range and the respective quality parameter, resulting in one Boolean comparison value per range and quality parameter, and
wherein a predetermined Boolean expression depending on the one Boolean comparison value is evaluated, wherein an alarm is triggered, when the predetermined Boolean expression returns logical true.

2. The computer-implemented method according to claim 1,
wherein historical sensor data is split into a plurality of intervals, wherein episodes of historical sensor data that are associated with error messages or inconsistencies are omitted.

3. The computer-implemented method according to claim 2,
wherein historical sensor data is split into a plurality of intervals, comprising 10000 intervals or more.

4. The computer-implemented method according to claim 1,
wherein a delay group is determined for a processing step as the minimum latency of a parameter change in that processing step to affect the outcome of the production subprocess, wherein current sensor data acquired within the latency of the respective delay group backwards from a current production time stamp is excluded from evaluation by the data-driven module.

5. The computer-implemented method according to claim 1,
wherein at least one feature comprises at least one time series describing a variation of at least one parameter of the sensor data along discrete time windows, wherein the machine-learning module performs a one-dimensional convolution of the at least one time series along a time axis.

6. The computer-implemented method according to claim 5,
wherein for a discrete time window at least one statistical parameter is determined as sample value of the at least one time series.

7. The computer-implemented method according to claim 6,
wherein the at least one statistical parameter comprises a mean value and/or a standard deviation value.

8. The computer-implemented method according to claim 1,
wherein validity and/or consistency of current sensor data is evaluated and optionally logged in the data repository by the preprocessing module.

9. The computer-implemented method according to claim 1,
wherein one quality parameter is a Z-strength of the paperboard.

10. The computer-implemented method according to claim 1,
wherein one quality parameter is a Scott bond of the paperboard.

11. The computer-implemented method according to claim 1,
wherein for the at least one quality parameter a first range is a set of invalid values lower than a lower valid limit, a second range is a set of valid values between the lower valid limit and an upper valid limit and a third range is a set of invalid values higher than the upper valid limit, wherein an alarm is triggered, when the probability value associated with the first range exceeds a predetermined first probability limit or when the probability value associated with the second range falls below a predetermined second probability limit or when the probability value associated with the third range exceeds a predetermined third probability limit.

12. A system, comprising:
at least one sensor,
a data repository, and
a computer,
wherein the at least one sensor is designed to acquire sensor data in a processing step of a processing pipeline comprising a paperboard production subprocess,
wherein the data repository is designed to receive and persistently store sensor data from the at least one sensor and to transfer sensor data towards the computer, and
wherein the computer implements the computer-implemented method according to claim 1.

13. The system according to claim 12,
wherein the data repository is formed as a cloud storage that can be accessed by an internet protocol based communication protocol stack.

14. The system according to claim 12, further comprising:
an alarm, wherein the alarm is designed to be triggered by the computer and to indicate a need of manual interaction with the paperboard production subprocess when being triggered.

15. A paperboard production machine designed to produce paperboard or a semi-product of paperboard, comprising:
the system according to claim 12.

* * * * *